US009125822B2

(12) United States Patent
Matsumoto et al.

(10) Patent No.: US 9,125,822 B2
(45) Date of Patent: Sep. 8, 2015

(54) PARTICLE FOR MEDICAL USE AND PROCESS FOR PRODUCING THE SAME

(75) Inventors: Takayuki Matsumoto, Tokyo (JP); Mitsutaka Matsumoto, Tokyo (JP); Yoshiaki Fukunishi, Tokyo (JP); Kazuya Kitagawa, Tokyo (JP); Yuzo Hamaguchi, Tokyo (JP)

(73) Assignee: SUMITOMO BAKELITE COMPANY, LTD., Tokyo (JP)

( * ) Notice: Subject to any disclaimer, the term of this patent is extended or adjusted under 35 U.S.C. 154(b) by 1458 days.

(21) Appl. No.: 11/992,582

(22) PCT Filed: Aug. 3, 2006

(86) PCT No.: PCT/JP2006/315375
§ 371 (c)(1),
(2), (4) Date: Mar. 26, 2008

(87) PCT Pub. No.: WO2007/037069
PCT Pub. Date: Apr. 5, 2007

(65) Prior Publication Data
US 2009/0246286 A1 Oct. 1, 2009

(30) Foreign Application Priority Data

Sep. 27, 2005 (JP) ................. 2005-279207
Jan. 31, 2006 (JP) ................. 2006-021939
Feb. 28, 2006 (JP) ................. 2006-053323
Mar. 28, 2006 (JP) ................. 2006-086867

(51) Int. Cl.
A61K 9/16 (2006.01)
B01J 20/26 (2006.01)
B01J 20/286 (2006.01)
B01J 20/32 (2006.01)
C08F 220/28 (2006.01)
C08F 220/36 (2006.01)
B01J 20/06 (2006.01)
B01J 20/10 (2006.01)

(52) U.S. Cl.
CPC .............. *A61K 9/1676* (2013.01); *B01J 20/06* (2013.01); *B01J 20/103* (2013.01); *B01J 20/26* (2013.01); *B01J 20/262* (2013.01); *B01J 20/264* (2013.01); *B01J 20/265* (2013.01); *B01J 20/286* (2013.01); *B01J 20/3204* (2013.01); *B01J 20/328* (2013.01); *B01J 20/3217* (2013.01); *B01J 20/3257* (2013.01); *B01J 20/3272* (2013.01); *B01J 20/3276* (2013.01); *B01J 20/3278* (2013.01); *B01J 20/3293* (2013.01); *C08F 220/28* (2013.01); *C08F 220/36* (2013.01)

(58) Field of Classification Search
None
See application file for complete search history.

(56) References Cited

U.S. PATENT DOCUMENTS

| 4,352,884 | A | 10/1982 | Nakashima et al. | |
| 4,634,604 | A | 1/1987 | Tlustakova et al. | |
| 4,778,909 | A | 10/1988 | Karger et al. | |
| 4,996,343 | A | 2/1991 | Karger et al. | |
| 5,019,370 | A * | 5/1991 | Jay et al. | 424/9.44 |
| 5,086,143 | A | 2/1992 | Sutton et al. | |
| 6,881,804 | B1 * | 4/2005 | Sellergren et al. | 526/219.6 |
| 2003/0013674 | A1 * | 1/2003 | Bednarski et al. | 514/44 |
| 2003/0028071 | A1 * | 2/2003 | Handy et al. | 600/12 |
| 2004/0018564 | A1 | 1/2004 | Kasai et al. | |
| 2004/0171808 | A1 * | 9/2004 | Kataoka et al. | 530/350 |
| 2004/0180096 | A1 * | 9/2004 | Prasad et al. | 424/490 |

FOREIGN PATENT DOCUMENTS

| EP | 1563847 | 8/2005 |
| JP | 56-115727 | 9/1981 |
| JP | 59-195153 | 11/1984 |
| JP | 60-252489 | 12/1985 |
| JP | 4-233924 | 8/1992 |
| JP | 8-208773 | 8/1996 |
| JP | 9-221618 | 8/1997 |
| JP | 2753762 | 3/1998 |
| JP | 2000-44807 | 2/2000 |
| JP | 2004-61301 | 2/2004 |
| JP | 2004-196770 | 7/2004 |
| JP | 2006-176720 | 7/2006 |
| WO | WO 2004024955 A1 * | 3/2004 |
| WO | WO 2006101798 A2 * | 9/2006 |

OTHER PUBLICATIONS

Nab Vieira, JR Neto, MT Tiera. "Synthesis, characterization and solution properties of amphiphilic N-isopropylacrylamide-poly(ethylene glycol)-dodecyl methacrylate thermosensitive polymers." Colloids and Suraces A: Physiochem. Eng. Aspects. vol. 262, 2005, pp. 251-259.*

LR Hirsch. "Diagnostic and Therapeutic Applications of Metal Nanoshells." Rice University, PhD Thesis. Mar. 2004. Title page, pp. i-x, and pp. 1-112.*

European Office Action for Application No. 06 782 235.3 dated Aug. 31, 2012.

* cited by examiner

*Primary Examiner* — Isaac Shomer
(74) *Attorney, Agent, or Firm* — Smith, Gambrell & Russell LLP.

(57) ABSTRACT

A main object of the invention is to provide a particle for medical use which has an excellent capability of fixing a target biologically active substance and has such chemical and physical stability that the particle is less dissolved or deteriorated in a washing step.

The present invention has solved the above problem with a particle for medical use having a layer containing a polymer compound formed on a surface of a core particle, wherein the polymer compound is a polymer comprising at least repeating units derived from an ethylenically unsaturated polymerizable monomer (a) having a functional group for fixing a biologically active substance, wherein the polymer has a reactive functional group on at least one terminal side thereof.

9 Claims, No Drawings

PARTICLE FOR MEDICAL USE AND PROCESS FOR PRODUCING THE SAME

TECHNICAL FIELD

The present invention relates to a particle for medical use having a function of fixing a biologically active substance, and a process for producing the same.

BACKGROUND ART

Polymer-coated particles composed of various kinds of particles and polymers have been widely used in the industrial field. In recent years, such polymer particles are increasingly important in the fields of medicine and fundamental biology. For example, there is growing interest in applications to affinity chromatography carriers, medical diagnosis, drug delivery system (DDS), and drug development. As an example of the application to drug development, biological molecules such as specific proteins are trapped by biologically active substances called ligands which have been fixed to various particles (carriers), and then the biological molecules are separated and refined.

A particle used as a carrier is required to satisfy the following conditions: (1) the particle has a functional group capable of fixing a large amount of ligand or spacer under a mild condition; (2) the carrier does not nonspecifically adsorb biological substances such as protein; (3) the particle has a mechanical strength suitable for the intended use. However, there is no carrier which satisfies these conditions.

The performance of a carrier largely depends on the amount of ligand to be fixed, so that a carrier is required to fix as much ligand as possible. The larger the amount of ligand is fixed, the larger the total amount of protein is trapped. In particular, when the target protein is a minor component among the proteins to be trapped by the ligand, the target protein may be not detected if the fixed amount is too small. Accordingly, particles capable of fixing a large amount of ligand have been demanded.

It is also very important to inhibit nonspecific adsorption of components other than the protein to be trapped. Among known carriers, inorganic carriers composed of silica gel particles are expected to be suitable for separation because they are porous and have high physical strength. However, silica gel particles have a disadvantage of causing high nonspecific adsorption, so that they are scarcely used for practical purposes. As synthetic polymer carriers, particles composed of a polyacrylamide gel (trade name: Bio-GelP, manufactured by Bio-Rad Laboratories, Inc.), polystyrene, or an ethylene-maleic anhydride copolymer have been developed. However, these polymers also have a disadvantage of being prone to nonspecific adsorption of biological substances.

As described above, when particles are used as medical carriers, their nonspecific adsorption often present problems. In order to avoid the problems, various techniques have been studied. An example is a blocking method wherein a target biologically active substance is attached to the particle surface, and then a harmless protein such as bovine serum albumin (BSA) is attached to the rest portion of the particle surface. However, the effect of the method is not sufficient. In another method, DNA which specifically binds to a specific protein is attached to particles having a surface composed of an epoxy group-containing resin, and the particles are used for refinement of the protein (for example, Patent Document 1). In the method, epoxy groups are introduced to the particle surface by glycidyl methacrylate or the like because it less exhibits nonspecific adsorption to proteins. However, direct binding between epoxy groups and a biologically active substance such as DNA requires significantly severe conditions. Therefore, the method is improper when the biologically active substance to be fixed is unstable toward alkalis and at high temperatures, because the biologically active substance may be deteriorated during the fixing process. As exemplified by the examples, when particles having a surface composed of an epoxy group-containing resin are synthesized by polymerization, the control of the particle size is difficult as with the case described in Patent Document 2. Particles having a core composed of a polymer compound cannot have higher specific gravity than those composed of an inorganic material, so that they are difficult to be separated and collected.

Another method for reducing nonspecific adsorption to particles is the synthesis of polymer particles with minimal nonspecific adsorption through emulsion polymerization or the like. For example, Patent Document 2 describes a method for producing copolymer particles through emulsion polymerization or suspension polymerization of an ethylenically unsaturated polymerizable monomer having a reactive group reacting with a biologically active substance, an ethylenically unsaturated polymerizable monomer having a polyoxyalkylene side chain, and an ethylenically unsaturated polymerizable vinyl aromatic monomer conferring hydrophobicity. However, with these methods, it is difficult to control the diameter of the resultant particles. In general, particles having a relatively uniform particle size are produced by emulsion polymerization, but the particle size is limited to the order of submicron. On the other hand, the particles produced by suspension polymerization have a large particle size distribution, so that they must be subjected to classification when used as, for example, a column filler. However, it is difficult to minutely classify the polymer particles without a special apparatus. In addition, the size of the obtained particles range from several tens to several hundreds of nanometers, and it is difficult to synthesize particles having a smaller diameter. Furthermore, particles obtained by polymerization are polymers, so that the strength of the carrier is inevitably limited. For applications where high strength is required, it is inevitably necessary to increase the particle strength by, for example, increasing the ratio of the ethylenically unsaturated polymerizable vinyl aromatic monomer in the polymer. However, this is disadvantages for nonspecific adsorption.

At present, most frequently used carriers are porous agarose particles (trade name: Sepharose) and dextran particles (trade name: Sephadex) accompanied by various functional groups. Agarose gel is said to be suitable for use with high molecular weight biological substances because it can remove higher molecular weight impurities in comparison with dextran or acrylamide. However, these carriers are less resistant to pressure because of their low physical strength, and have many other problems such as unavoidable inclusion of impurities caused by adsorption or retention of impurities in the network structure of the carrier.

[Patent Document 1] Japanese Patent No. 2753762
[Patent Document 2] Japanese Patent No. 3215455

DISCLOSURE OF THE INVENTION

Problem to be solved by the Invention

An object of the present invention is to provide a particle for medical use and a process for producing the same, wherein the particle has an excellent capability of fixing a biologically active substance and has such chemical and physical stability that the particle is less dissolved or deteriorated in a washing step. Another object of the present invention is to provide a particle for medical use and a process for producing the same, wherein the particle has the above characteristics, in addition, less exhibits nonspecific adsorption to proteins and others, and provides a high SN ratio.

Means for Solving the Problem

The inventors have studied earnestly in order to develop a particle for medical use which is excellent in capability of fixing a target biologically active substance and less exhibits nonspecific adsorption to other components. As a result, the inventors have found out that: a particle in which a layer containing a polymer compound is formed on the surface of the core particle, wherein the polymer compound is a polymer including at least repeating units derived from an ethylenically unsaturated polymerizable monomer (a) having a functional group for fixing a biologically active substance and has a reactive functional group on at least one terminal side thereof, is excellent in capability of fixing the biologically active substance, has such chemical and physical stability that the particle is less dissolved or deteriorated in a washing step; and the nonspecific adsorption of proteins and the like to the particle for medical use can be further decreased by adding repeating units derived from an ethylenically unsaturated polymerizable monomer (b) having an alkylene glycol residue to the repeating units of the polymer compound. Thus, the present invention has been accomplished.

Accordingly, the present invention is:

(1) a particle for medical use having a layer comprising a polymer compound formed on a surface of a core particle, wherein the polymer compound is a polymer comprising at least repeating units derived from an ethylenically unsaturated polymerizable monomer (a) having a functional group for fixing a biologically active substance, wherein the polymer has a reactive functional group on at least one terminal side thereof;

(2) a particle for medical use having a layer comprising a polymer compound formed on a surface of a core particle, wherein the polymer compound is a copolymer comprising at least repeating units derived from an ethylenically unsaturated polymerizable monomer (a) having a functional group for fixing a biologically active substance, and an ethylenically unsaturated polymerizable monomer (b) having an alkylene glycol residue, wherein the copolymer has a reactive functional group on at least one terminal side thereof;

(3) a particle for medical use having a layer comprising a polymer compound formed on a surface of a core particle, wherein the polymer compound is a copolymer comprising at least repeating units derived from an ethylenically unsaturated polymerizable monomer (a) having a functional group for fixing a biologically active substance, an ethylenically unsaturated polymerizable monomer (b) having an alkylene glycol residue, and an ethylenically unsaturated polymerizable monomer (c) having a hydrophobic group, wherein the copolymer has a reactive functional group on at least one terminal side thereof;

(4) the particle for medical use according to any one of (1) to (3), wherein at least a portion of the reactive functional group is covalently bonded to the surface of the particle;

(5) the particle for medical use according to any one of (1) to (4), wherein at least one terminal side of the polymer or copolymer is represented by the following general formula [1]:

[Formula 1]

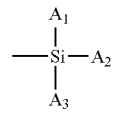

wherein at least one of $A_1$, $A_2$, and $A_3$ is a reactive moiety, and the others are each an alkyl group;

(6) the particle for medical use according to (5), wherein the reactive moiety in the general formula [1] is an alkoxyl group;

(7) the particle for medical use according to any one of (1) to (6), wherein the functional group of the ethylenically unsaturated polymerizable monomer (a) having a functional group for fixing a biologically active substance is at least one functional group selected from an aldehyde group, an active ester group, an epoxy group, a vinylsulfone group, and biotin;

(8) the particle for medical use according to any one of claims 1 to 7, wherein the ethylenically unsaturated polymerizable monomer (a) having a functional group for fixing a biologically active substance is a monomer having an active ester group and represented by the following general formula [2]:

[Formula 2]

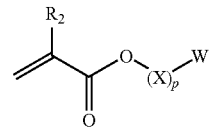

wherein $R_2$ represents a hydrogen atom or a methyl group, X represents an alkyl group or an alkylene glycol residue having 1 to 10 carbon atoms, W represents an active ester group, and p represents an integer from 1 to 100, and the repeated Xs may be the same or different when p is an integer of 2 or more and 100 or less;

(9) the particle for medical use according to (8), wherein the active ester group is a p-nitrophenyl ester or N-hydroxysuccinimide ester;

(10) the particle for medical use according to any one of (2) to (9), wherein the ethylenically unsaturated polymerizable monomer (b) having an alkylene glycol residue is a monomer represented by the following general formula [3]:

[Formula 3]

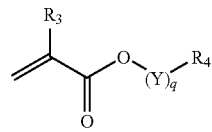

wherein $R_3$ represents a hydrogen atom or a methyl group, $R_4$ represents a hydrogen atom or an alkyl group having 1 to 20 carbon atoms, Y represents an alkylene glycol residue having 1 to 10 carbon atoms, and q represents an integer from 1 to 100, the repeated Ys may be the same or different;

(11) the particle for medical use according to any one of (2) to (10), wherein the ethylenically unsaturated polymerizable monomer (b) having an alkylene glycol residue is methoxypolyethylene glycol (meth)acrylate or ethoxypolyethylene glycol (meth)acrylate;

(12) the particle for medical use according to (11), wherein an average repeating number of the ethylene glycol residue of the methoxypolyethylene glycol (meth)acrylate or ethoxypolyethylene glycol (meth)acrylate is from 3 to 100;

(13) the particle for medical use according to any one of (3) to (12), wherein the hydrophobic group of the ethylenically unsaturated polymerizable monomer (c) having a hydrophobic group is an alkyl group;

(14) the particle for medical use according to any one of (3) to (13), wherein the hydrophobic group of the ethylenically unsaturated polymerizable monomer (c) having a hydrophobic group is an alkyl group having 3 to 20 carbon atoms;

(15) the particle for medical use according to (14), wherein the ethylenically unsaturated polymerizable monomer (c) having a hydrophobic group is at least one monomer selected from n-butyl methacrylate, n-dodecyl methacrylate, n-octyl methacrylate, and cyclohexyl methacrylate;

(16) the particle for medical use according to any one of (1) to (15), wherein the core particle is made of an inorganic material;

(17) the particle for medical use according to (16), wherein the inorganic material is composed of inorganic oxide;

(18) the particle for medical use according to (17), wherein the surface of the inorganic oxide is treated with alkoxysilane;

(19) the particle for medical use according to (18), wherein the alkoxysilane comprises tetraalkoxysilane;

(20) the particle for medical use according to (19), wherein the tetraalkoxysilane is at least one selected from tetramethoxysilane, tetraethoxysilane, tetrapropoxysilane, and tetrabutoxysilane;

(21) the particle for medical use according to (19), wherein the tetraalkoxysilane comprises tetraethoxysilane;

(22) the particle for medical use according to any one of (17) to (21), wherein the inorganic oxide is silicon oxide or titanium oxide;

(23) a process for producing a particle for medical use defined by any one of (1) to (22) comprising a step of directly applying the polymer compound to a surface of a core particle;

(24) a process for producing a particle for medical use defined by any one of (1) to (22), which comprises steps of dissolving the polymer compound in a solvent to prepare a solution, applying the solution to a surface of a core particle, and drying the coating;

(25) the process for producing a particle for medical use according to (24), wherein the solution comprises 5% by weight or more of the polymer compound;

(26) the process for producing a particle for medical use according to (24) or (25), wherein the step of applying the solution to the core particle further comprises steps of making a mixture comprising the solution and the core particle, and removing a portion of the solvent under atmospheric pressure or reduced pressure;

(27) the process for producing a particle for medical use according to any one of (23) to (26), which further comprises a step of treating the surface of the particle with alkoxysilane before the step of applying the polymer compound or the solution to the surface of a core particle;

(28) the process for producing a particle for medical use according to (27), wherein the step of treating the surface of the particle with alkoxysilane further comprises steps of stirring and mixing the particle and the alkoxysilane in a solution containing an alkali catalyst, drying, and stirring in an aqueous solution containing an acid;

(29) the process for producing a particle for medical use according to (28), wherein the acid is an inorganic acid;

(30) the process for producing a particle for medical use according to (29), wherein the inorganic acid is hydrochloric acid;

(31) the process for producing a particle for medical use according to any one of (23) to (30), which further comprises a step of heating treatment after the step of applying the polymer compound or the solution to the surface of the core particle;

(32) the process for producing a particle for medical use according to any one of (23) to (31), wherein the solvent comprises cyclohexanone, and the core particle is composed of silicon oxide.

Effect of the Invention

According to the present invention, it is possible to provide a particle for medical use which has an excellent capability of fixing a target biologically active substance and has such chemical and physical stability that the surface layer containing a polymer compound is less dissolved or deteriorated in a washing step. By adding, to the repeating units of the polymer compound, an ethylenically unsaturated polymerizable monomer (b) having an alkylene glycol residue, it is possible to provide a particle for medical use to which proteins are less subjected to nonspecific adsorption. In the particle for medical use of the present invention, the core particle can be arbitrarily selected, which facilitates the control of the diameter and strength of the particle.

BEST MODE FOR CARRYING OUT THE PRESENT INVENTION

The particle of the present invention has a layer comprising a polymer compound formed on a surface of a core particle, wherein the polymer compound is a polymer compound for medical material which is a polymer or a copolymer comprising at least repeating units derived from an ethylenically unsaturated polymerizable monomer (a) having a functional group for fixing a biologically active substance, and has a reactive functional group on at least one terminal side thereof. This polymer compound has a nature of fixing a specific biologically active substance. Furthermore, the compound has a reactive functional group on at least one terminal side thereof; thus, the compound becomes able to form a covalent bond to a surface of a core particle, thereby making it possible to cause the polymer compound to be grafted onto the surface of the core particle. The thus-obtained grafted particle has such high stability that the polymer compound does not flow out therefrom in a washing step. Furthermore, when thereto are added repeating units derived from an ethylenically unsaturated polymerizable monomer (b) having an alkylene glycol residue, as a component of the polymer compound, the alkylene glycol residue performs a function of inhibiting the nonspecific adsorption of proteins. Accordingly, the nature of inhibiting the nonspecific adsorption of a biologically active substance is improved.

Moreover, the amount of the polymer compound to be grafted is uniformly increased by activating the surface of the core particle before the polymer compound is grafted to the particle surface. This increases the amount of the biologically active substance fixed to the obtained grafted particle. Furthermore, the particle of the present invention has a layer containing a polymer compound on the surface of the core particle, and the size and strength of the particle can be appropriately controlled by appropriately selecting the core particle. For example, the core particle may be an inorganic material having a high specific gravity thereby facilitating separation and collection of the product.

In the ethylenically unsaturated polymerizable monomer (a) having a functional group for fixing a biologically active substance to be used in the invention, the functional group may be a chemically active group, receptor group or ligand group, but is not limited thereto. Specific examples thereof include an aldehyde group, an active ester group, an epoxy group, a vinylsuflone group, biotin, a thiol group, an amino group, an isocyanate group, an isothiocyanate group, a hydroxyl group, an acrylate group, a maleimide group, a hydrazide group, an azide group, an amide group, a sulfonate group, streptavidin, and metal chelates. Among them, preferred are an aldehyde group, an active ester group, an epoxy group, and a vinylsulfone group from the viewpoint of the reactivity thereof with an amino group, which is contained in an biologically active substance in many cases. Moreover, biotin is preferred since it has a high binding constant onto a biologically active substance. In particular, an active ester group is most preferred from the viewpoint of the storage stability of the monomer.

The ethylenically unsaturated polymerizable monomer (a) having a functional group for fixing a biologically active substance to be used in the invention is not particularly limited about the structure thereof. The monomer (a) is preferably a compound represented by a general formula [2] illustrated below, wherein a (meth) acrylic group and an active ester group are bonded to each other through a chain of an alkyl group or an alkylene glycol residue which has 1 to 10 carbon atoms. In particular, a chain of an alkylene glycol residue itself has a nature of inhibiting the nonspecific adsorption of proteins. For this reason, a monomer wherein a (meth)acrylic group and an active ester group are bonded to each other through a chain of an alkylene glycol residue has both of a nature of fixing a biologically active substance and a nature of inhibiting the nonspecific adsorption of proteins. Accordingly, even if a polymer from such a monomer is a homopolymer, the polymer can be preferably used as a polymer compound for forming a layer on the surface of the particle for medical use as long as the polymer has, on at least one terminal side thereof, a reactive functional group. In the invention, (meth)acrylic means acrylic and/or methacrylic, and (meth)acrylate means acrylate and/or methacrylate.

[Formula 4]

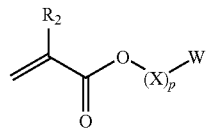

[2]

wherein $R_2$ represents a hydrogen atom or a methyl group, X represents an alkyl group or an alkylene glycol residue having 1 to 10 carbon atoms, W represents an active ester group, and p represents an integer from 1 to 100, and the repeated Xs may be the same or different when p is an integer of 2 or more and 100 or less.

When X is an alkylene glycol residue in the formula [2], X has 1 to 10 carbon atoms, preferably 1 to 6 carbon atoms, more preferably 2 to 4 carbon atoms, even more preferably 2 to 3 carbon atoms, most preferably 2 carbon atoms. The alkylene glycol residue referred to herein means an alkyleneoxy group (—R—O, wherein R is an alkylene group) which remains after a hydroxyl group at a single terminal or hydroxyl groups at both terminals of an alkylene glycol (HO—R—OH wherein R is the alkylene group) are subjected to condensation reaction with a different compound. For example, in the case of methylene glycol (OH—$CH_2$—OH), the alkylene glycol residue is a methylene oxy group (—$CH_2$—O—); and in the case of ethylene glycol (OH—$CH_2CH_2$—OH), the alkylene glycol residue is an ethyleneoxy group (—$CH_2CH_2$—O—).

The repeating number p of Xs is an integer from 1 to 100. When X is an alkylene glycol residue, the number p is more preferably an integer from 2 to 90, even more preferably an integer from 2 to 80. In the case of a mixture of polymer compound species the numbers p's of which are various, the number p of the entire species of the polymer compound is specified as the average value of the above. When the repeating number p is 2 or more, the repeated Xs may be the same or different.

When Xs are each an alkyl group in the formula [2], the total number $((X)_p)$ of the carbon atoms in the alkyl groups the number of which is p is preferably from 1 to 100, more preferably from 1 to 20. The alkyl group is not particularly limited about the structure thereof, and may be linear, branched or cyclic.

The "active ester group" used in the invention means an ester group activated relative to a nucleophilic reaction by having a high acidic electron attracting group as one substituent of the ester group, that is an ester group having a high reaction activity, which is conventionally used in various chemical synthesis such as in a field of polymer chemistry, or in a field of peptide synthesis. Actually, phenol esters, thiophenol esters, N-hydroxyamine esters, esters of a heterocyclic hydroxy compound and so on are each known as an active ester group having a much higher activity than that of alkyl esters or the like.

Such an active ester group may be an ester wherein R" in —COOR" has the above-mentioned high acidic electron attracting group. Examples thereof include a p-nitrophenyl active ester group, wherein R" is p-nitrophenyl; an N-hydroxysuccinimide active ester group, wherein R" is N-hydroxysuccinimide; a phthalic imide active ester group, wherein R" is phthalic imide; and a 5-norbornene-2,3-dicarboxylmide active ester group, wherein R" is 5-norbornene-2,3-dicarboxylmide. In particular, a p-nitrophenyl active ester group or N-hydroxysuccinimide active ester group is preferred from the viewpoint of height in storage stability and reactivity, and balance therebetween. A p-nitrophenyl active ester group is most preferred.

Examples of the ethylenically unsaturated polymerizable monomer (a) having a functional group for fixing a biologically active substance include p-nitrophenyloxycarbonyl-poly(ethylene glycol)(meth)acrylate, and succinimideoxycarbonyl-poly(ethylene glycol)(meth)acrylate. In particular, p-nitrophenyloxycarbonyl-poly(ethylene glycol)(meth)acrylate represented by a formula illustrated below is preferred. The repeating number p of the ethylene glycols and/or the average value of p is preferably from 2 to 20.

[Formula 5]

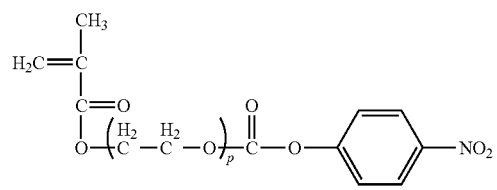

In the polymer compound of the invention, the ratio of portions derived from the ethylenically unsaturated polymerizable monomer (a) having a functional group for fixing a biologically active substance is not particularly limited, and is preferably from 1 to 99.7% by mol of the total number of repeating units of all monomers in the polymer, more preferably form 1 to 80% by mol thereof, most preferably from 1 to 70% by mol thereof.

The ethylenically unsaturated polymerizable monomer (b) having an alkylene glycol residue to be used in the invention is not particularly limited about the structure thereof, and is preferably a compound represented by a general formula [3] illustrated below, which is composed of a (meth) acrylic group and a chain of an alkylene glycol residue Y having 1 to 10 carbon atoms.

[Formula 6]

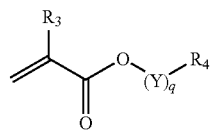

[3]

wherein $R_3$ represents a hydrogen atom or a methyl group, $R_4$ represents a hydrogen atom or an alkyl group having 1 to 20 carbon atoms, Y represents an alkylene glycol residue having 1 to 10 carbon atoms, and q represents an integer from 1 to 100, the repeated Ys may be the same or different when q is an integer of 2 or more and 100 or less.

The alkylene glycol residue Y in the formula [3] has 1 to 10 carbon atoms, preferably 1 to 6 carbon atoms, more preferably 2 to 4 carbon atoms, even more preferably 2 to 3 carbon atoms, most preferably 2 carbon atoms. The repeating number q of the alkylene glycol residues Ys is not particularly limited, and is preferably an integer from 1 to 100, more preferably from an integer from 2 to 100, even more preferably an integer from 2 to 95, most preferably an integer from 20 to 90. In the case of a mixture of polymer compound species the numbers q's of which are various, the number q of the entire species of the polymer compound is specified as the average value of the above. When the repeating number q is 2 or more, Ys may be the same or different.

Examples of the ethylenically unsaturated polymerizable monomer (b) having an alkylene glycol residue include methoxy polyethylene glycol (meth)acrylate, ethoxy polyethylene glycol (meth)acrylate, 2-hydroxyethyl (meth)acrylate and an ester wherein the hydroxyl group thereof is mono-substituted, 2-hydroxypropyl (meth)acrylate and an ester wherein the hydroxyl group thereof is mono-substituted, 2-hydroxybutyl (meth)acrylate and an ester wherein the hydroxyl group thereof is mono-substituted, glycerol mono(meth)acrylate, (meth)acrylate having polypropylene glycol as its side chain, 2-methoxyethyl (meth)acrylate, 2-ethoxyethyl (meth)acrylate, methoxydiethylene glycol (meth)acrylate, ethoxydiethylene glycol (meth)acrylate, and ethoxypolyethylene glycol (meth)acrylate. Preferred is methoxypolyethylene glycol (meth)acrylate. Preferred is methoxypolyethylene glycol methacrylate or ethoxypolyethylene glycol meth) acrylate since the nonspecific adsorption of components other than the target biologically active substance is less caused and the (meth)acrylate is easily available. In particular, methoxy-polyethylene glycol (meth)acrylate or ethoxypolyethylene glycol (meth)acrylate wherein the average repeating number of ethylene glycol residues is from 3 to 100 is preferably used since the (meth)acrylate is good in handleability when synthesized.

In the polymer compound used for the surface of the particle of the invention, the ratio of portions derived from the ethylenically unsaturated polymerizable monomer (b) having an alkylene glycol residue is not particularly limited, and is preferably from 0 to 95% by mol of the total number of repeating units of all monomers in the polymer, more preferably from 30 to 95% by mol thereof, most preferably from 50 to 90% by mol thereof.

The polymer compound used for the surface of the particle of the invention may contain another ethylenically unsaturated polymerizable monomer other than the ethylenically unsaturated polymerizable monomer (a) having a functional group for fixing a biologically active substance and the ethylenically unsaturated polymerizable monomer (b) having an alkylene glycol residue as long as the polymer compound has, on at least one terminal side thereof, a reactive functional group. The polymer compound may be a polymer compound obtained by copolymerizing an ethylenically unsaturated polymerizable monomer (c) having a hydrophobic group further therewith since the polymer compound has an improved coatability onto, for example, a plastic particle. The ethylenically unsaturated polymerizable monomer (c) having a hydrophobic group is not particularly limited about the structure thereof as long as the monomer has a hydrophobic group without having any functional group of fixing a biologically active substance nor any alkylene glycol residue. The hydrophobic group may be a linear, branched or cyclic aliphatic hydrocarbon group, an aromatic hydrocarbon group, or the like. The ethylenically unsaturated polymerizable monomer (c) having a hydrophobic group is preferably a monomer wherein a hydrophobic group is bonded to a (meth)acrylic group ($CH_2$=$CR_5$—COO— wherein $R_5$ represents a hydrogen atom or a methyl group). The monomer may be a (meth)acrylate to which an aliphatic hydrocarbon is bonded, or a (meth)acrylate to which an aromatic hydrocarbon is bonded. The monomer is more preferably a (meth)acrylate wherein the hydrophobic group is an alkyl group. The monomer is even more preferably a (meth)acrylate wherein the alkyl group is an alkyl group having 3 to 20 carbon atoms. The alkyl group is not particularly limited about the structure thereof, and may be linear, branched or cyclic.

Specific examples of the monomer include n-butyl (meth)acrylate, iso-butyl (meth)acrylate, sec-butyl (meth)acrylate, t-butyl (meth)acrylate, n-neopentyl (meth)acrylate, iso-neopentyl (meth)acrylate, sec-neopentyl (meth)acrylate, neopentyl (meth)acrylate, n-hexyl (meth)acrylate, iso-hexyl (meth)acrylate, heptyl (meth)acrylate, n-octyl (meth)acrylate, iso-octyl (meth)acrylate, 2-ethylhexyl (meth)acrylate, n-nonyl (meth)acrylate, iso-nonyl (meth)acrylate, n-decyl (meth)acrylate, iso-decyl (meth)acrylate, n-dodecyl (meth)acrylate, iso-dodecyl (meth)acrylate, n-tridecyl (meth)acrylate, iso-tridecyl (meth)acrylate, n-tetradecyl (meth)acrylate, iso-tetradecyl (meth)acrylate, n-pentadecyl (meth)acrylate, iso-pentadecyl (meth)acrylate, n-hexadecyl (meth)acrylate, iso-hexadecyl (meth)acrylate, n-octadecyl (meth)acrylate, iso-octadecyl (meth)acrylate, cyclohexyl (meth)acrylate, and isobornyl (meth)acrylate. Among them, most preferred are n-butyl methacrylate, n-dodecyl methacrylate, n-octyl methacrylate, and cyclohexyl methacrylate.

In the polymer compound used in the invention, the ratio of portions derived from the ethylenically unsaturated polymerizable monomer (c) having a hydrophobic group is not particularly limited, and is preferably from 0 to 90% by mol of the total number of repeating units of all monomers in the polymer, more preferably from 0 to 80% by mol thereof, most preferably from 0 to 70% by mol thereof. If the composition ratio of the ethylenically unsaturated polymerizable monomer (c) in the polymer is more than the upper limit, it is feared that the amount of the target biologically active substance to be fixed decreases, and nonspecific adsorption of unintended components may increase during trapping of a specific protein by the biologically active substance.

The reactive functional group introduced into at least one terminal side of the polymer is not particularly limited as long as the group is a functional group which can be covalently bonded to a surface of a core particle. In accordance with a functional group present on the surface of the used particle, a reactive functional group which can be covalently bonded thereto can be appropriately selected. As will be described later, since the material of the core particle used in the present invention may be an organic or inorganic material, an alkoxysilyl group, a hydroxyl group, an amino group, an aldehyde group, a carboxyl group, or the like can be introduced to the surface thereof. Thus, the reactive functional group introduced to the terminal can be, for example, a reactive silyl group or an amino group.

In particular, the reactive functional group introduced into at least one terminal side of the polymer is preferably a reactive silyl group since the group can be caused to react with the substrate under a relatively mild condition. The reactive silyl group is a functional group which generates a silanol group by hydrolysis, a silanol group, or the like. The functional group which generates a silanol group by hydrolysis is a group which is easily hydrolyzed when it contacts water, so that a silanol group is generated. The reactive silyl group may be a structure represented by the following general formula [1]. In particular, it is preferred that the terminal has the structure represented by the following formula [5] introduced by the mercapto compound described below:

[Formula 7]

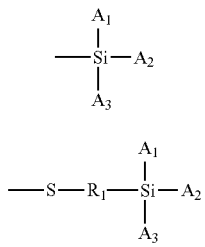

wherein in the formulae [1] and [5], at least one of $A_1$, $A_2$, and $A_3$ is a reactive moiety, and the others are each an alkyl group. The reactive moiety is a moiety which can be covalently bonded to a substrate. Examples of the reactive moiety include an alkoxyl group, a halogen group, an amino group, a isocyanate group, a phenoxy group, and a hydroxyl group. In the formula [5], $R_1$ represents an alkyl group having 1 to 20 carbon atoms, more preferably an alkyl group having 1 to 5 carbon atoms, and most preferably an alkyl group having 1 to 3 carbon atoms.

Preferred examples of the reactive functional group include a halogenated silyl group (≡Si—X wherein X is a halogen group), an alkoxysilyl group (≡Si—OR wherein R is an alkyl group), a phenoxysilyl group (≡Si—OPh wherein Ph is a phenyl group), and an acetoxysilyl group (≡Si—OOCCH₃). An alkoxysilyl group, a phenoxysilyl group, and an acetoxysilyl group are preferred since they contain no halogen. Among them, an alkoxysilyl group is in particular preferred since the group easily generates a silanol group.

The introduction ratio of the reactive functional group introduced into at least one terminal side of the polymer is preferably from 0.2 to 10% by mol of the total number of the repeating units of all monomers in the polymer, more preferably from 0.5 to 5% by mol thereof.

About the polymer compound used for the surface of the particle of the invention, the method for introducing the reactive functional group into the terminal is not particularly limited, and is preferably a method of subjecting at least the ethylenically unsaturated polymerizable monomer (a) having a functional group for fixing a biologically active substance to radical polymerization in the presence of a mercapto compound (d) having a reactive functional group in a solvent since this method is simple and easy. If necessary, the ethylenically unsaturated polymerizable monomer (b) having an alkylene glycol residue or the ethylenically unsaturated polymerizable monomer (c) having a hydrophobic group may be copolymerized. Since the mercapto compound (d) having a reactive functional group acts as a chain transfer agent, a polymer compound having a reactive functional group at its terminal is obtained. The mercapto compound (d) having a reactive functional group is not particularly limited, and is preferably a mercaptosilane compound represented by the following general formula [4]:

[Formula 8]

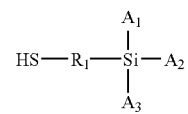

wherein $R_1$, is an alkyl group having 1 to 20 carbon atoms, more preferably 1 to 5 carbon atoms, most preferably 1 to 3 carbon atoms, at least one of $A_1$, $A_2$ and $A_3$ is a reactive moiety of a reactive functional group, and the others are each an alkyl group. Examples of the reactive moiety include an alkoxy group, a halogen group, an amino group, a isocyanate group, a phenoxy group, and a hydroxyl group. In particular, an alkoxy group is most preferred since the group easily generates a silanol group. It is preferred that only one reactive moiety is present in the reactive functional group in view of storage stability.

Examples of the mercaptosilane compound having an alkoxyl group include (3-mercaptopropyl)trimethoxysilane, (3-mercaptopropyl)methyldimethoxysilane, (3-mercaptopropyl)dimethylmethoxysilane, (3-mercaptopropyl)triethoxysilane, (3-mercaptopropyl)methyldiethoxysilane, (3-mercaptopropyl)dimethylethoxysilane, (mercaptomethyl)trimethoxysilane, (mercaptomethyl)methyldimethoxysilane, (mercaptomethyl)dimethylmethoxysilane, (mercaptomethyl)triethoxysilane, (mercaptomethyl)methyldiethoxysilane, and (mercaptopropyl)dimethylethoxysilane. From the viewpoint of availability, (3-mercaptopropyl)trimethoxysilane and (3-mercaptopropyl)triethoxysilane are preferred. These mercaptosilane compounds are used alone or in combination of two or more thereof.

The solvent is not limited to any special solvent insofar as each of ethylenically unsaturated polymerizable monomers and the mercapto compound (d) having a reactive functional group can be dissolved therein. Examples thereof include alcohols such as methanol, ethanol, isopropanol, n-butanol, t-butyl alcohol, and n-pentanol, benzene, toluene, tetrahydrofuran, dioxane, dichloromethane, chloroform, cyclohexanone, N,N-dimethylformamide, dimethyl sulfoxide, methyl acetate, ethyl acetate, butyl acetate, methyl ethyl ketone, methyl butyl ketone, ethylene glycol monoethyl ether, ethylene glycol monomethyl ether, and ethylene glycol monobutyl ether. These solvents are used alone or in combination of two or more thereof.

The polymerization initiator may be any ordinary radical initiator. Examples thereof include azo compounds such as 2,2'-azobisisobutylnitrile (hereinafter referred to as "AIBN") and 1,1'-azobis(cyclohexane-1-carbonitrile), and organic peroxides such as benzoyl peroxide, and lauryl peroxide.

About the chemical structure of the polymer compound used for the surface of the particle of the invention, the bonding manner thereof in the case that the polymer is a copolymer may be any manner, such as a random, block or graft manner, as long as the copolymer is a copolymer which contains repeating units derived from at least the individual ethylenically unsaturated polymerizable monomers having a functional group for fixing a biologically active substance and which has a reactive functional group on at least one terminal thereof.

About the molecular weight of the polymer compound used for the surface of the particle of the invention, the number-average molecular weight is preferably 5,000 or more and 1,000,000 or less, more preferably 10,000 or more and 500,000 or less since the polymer compound is uniformly applied onto a substrate with ease and further the polymer compound is easily separated and purified from the ethylenically unsaturated polymerizable monomer(s) unreacted. The number-average molecular weight referred to herein is a number-average molecular weight calculated from the composition obtained by analysis of NMR measurement on the supposition that a reactive functional group is introduced into a single terminal of each of the polymer molecules.

The method for forming the layer containing the polymer compound on the surface of the core particle is not particularly limited. For example, the polymer compound itself or a solution of the polymer compound dissolved in a solvent is applied to the surface of the core particle by a known method such as immersion or spraying, and then the coating is dried at room temperature or under heating. In the present invention, the "layer" formed on the particle surface refers to a coating covering the entire surface of the core particle, and a coating covering at least a portion of the surface of the core particle.

The concentration of the polymer compound in the polymer compound solution is not particularly limited, but preferably 0.05% by weight or more, more preferably 0.3 to 70% by weight, even more preferably 1 to 50% by weight, and most preferably 5 to 50% by weight. If the concentration of the polymer compound in the polymer compound solution is below the lower limit, the amount of the polymer compound applied to the surface of the core particle decreases. Resultingly, the amount of the fixed biologically active substance decreases, and the capability of fixing the specific protein decreases. Furthermore, when the polymer compound includes repeating units derived from an ethylenically unsaturated polymerizable monomer (b) having an alkylene glycol residue, the effect of inhibiting nonspecific adsorption of proteins and the like to the particle for medical use decreases. From these facts, if the concentration of the polymer compound solution is below the lower limit, the effect of selectively trapping the specific protein may not be sufficiently achieved.

When the polymer compound is applied to the particle, the concentration of the polymer compound solution may be adjusted in advance at a specific concentration. Alternatively, the polymer compound solution may be concentrated during application to the particle. When a dilute solution of the polymer compound is applied to the particle, the viscosity of the solution is so low that the solution readily penetrates through the surface of a particle having fine geometry with micropores or the like. This is advantageous in impregnating the particle surface with the polymer compound solution, but the particle surface may be not thoroughly covered with the polymer compound because of the low concentration of the solution. On the other hand, when a concentrated solution of the polymer compound is used, the amount of the polymer compound applied to the particle surface is expected to increase, but the wettability of the particle with the solution decreases because of the increase of the surface tension of the solution, which results in the deterioration of workability. Accordingly, when beads having a complicated surface geometry are covered as much as possible with the polymer compound, it is preferred that a dilute solution of the polymer compound be applied while concentrating the solution. The method for concentration is not particularly limited, and may be any optional method such as heating evaporation or vacuum concentration.

The solvent is not limited to any special solvent insofar as the polymer compound can be dissolved therein. Examples thereof include alcohols such as ethanol, methanol, isopropanol, n-butanol, t-butyl alcohol, n-pentanol, and cyclohexanol, benzene, toluene, tetrahydrofuran, dioxane, dichloromethane, chloroform, acetone, methyl acetate, ethyl acetate, butyl acetate, methyl ethyl ketone, methylbutyl ketone, ethylene glycol monoethyl ether, ethylene glycol monomethyl ether, ethylene glycol monobutyl ether, and cyclohexanone. These solvents are used alone or in combination of two or more thereof. When the polymer compound has an alkoxysilyl group at its terminal, ethanol and methanol are preferred in view of inhibiting condensation between polymer compounds and being readily dried.

Conditions for covalently bonding the terminal reactive functional group of the polymer compound to the functional group on the surface of the core particle may be selected arbitrarily in accordance with the functional group. In the case that the polymer compound is, for example, a polymer compound having an alkoxysilyl group at its terminal, a silanol group generated by the hydrolysis undergoes dehydration condensation with a hydroxyl group, an amino group, a carbonyl group, a silanol group or the like on the surface of the core particle, so as to form covalent bonds. The covalent bonds formed by the dehydration condensation of the silanol group have a nature that the bonds are not easily hydrolyzed. Thus, the polymer compound grafted on the surface of the core particle is not easily dissolved or separated from the core particle. The dehydration condensation of the silanol group is promoted by heating treatment. The heating treatment is preferably in the range of temperatures at which the polymer compound is not denatured by heat, for example, in the range of 60 to 180° C. for 5 minutes to 24 hours.

Whether at least a portion of the reactive functional group at the terminal of the polymer compound is covalently bonded to the surface of the core particle can be determined usually from the reaction conditions according to an empirical rule known in the art. When the covalent bond is experimentally confirmed, as described in the following Examples, the particle is washed with a good solvent for the polymer compound, and then treated with, for example, an aqueous alkali solution. If liberation of the functional group for fixing a biologically active substance is confirmed, it can be determined that the polymer compound is covalently bonded to the particle surface. Alternatively, the covalent bond between the polymer compound and the particle surface may be confirmed, for example, by solid NMR.

In the case that an organic solvent having a high polarity such as ethanol or methanol is used or the hydrophilicity of the polymer compound itself is high, the alkoxysilyl group at the polymer terminal is hydrolyzed by water contained in the solvent or water in the air after the solution is applied. In many cases, therefore, the polymer compound can be grafted only by heating the particle without need of any special hydrolysis step. When the hydrolysis is insufficient, it is allowable to use a mixed solution wherein water is incorporated into an organic solvent. Theoretically, a sufficient result is produced when water necessary for generating a silanol group is supplied; however, the water content is preferably 15% or less by weight, considering easiness of the preparation of the solution. If the water content is large, it is feared that the polymer compound is not dissolved in the solvent.

The material of the core particle used in the present invention is not particularly limited, and may be an organic or inorganic material. Examples of organic carriers include porous agarose particles (trade name: Sepharose) and dextran particles (trade name: Sephadex) used as carriers for affinity chromatography, and other particles composed of a polyacrylamide gel (tradename: Bio-GelP, manufactured by Bio-Rad Laboratories, Inc.), polystyrene, an ethylene-maleic anhydride copolymer, and polymethyl methacrylate. Regarding inorganic materials, inorganic oxides are preferred to make particles having high strength. In particular, silicon oxide and titanium oxide are most preferred due to their handling ability. The size of the particles is not particularly limited, and may be appropriately selected according to the intended use. More specifically, the particle for medical use having an intended size can be produced by appropriately selecting the size of the core particle. This brings a big advantage over production of particles by emulsion polymerization or suspension polymerization wherein the control of particle size is difficult. When the particle is used as a practical medical material, the particle size is preferably from several nanometers to about 100 µm, though the preferred size varies according to intended use. Furthermore, when the core particle is made of an inorganic material, the specific gravity of the particle increases, which facilitates separation and collection of the product in comparison with a particle composed of an organic material.

When the polymer compound used in the present invention is grafted on the surface of the core particle, functional groups on the particle surface which reacts with the polymer compound can be used for the grafting. If such functional groups are absent or insufficient, it is preferable to activate the surface of the core particle. The method for the activation is not particularly limited, and examples of the method include surface treatment with alkoxy silane, acid or alkaline treatment, plasma treatment in the atmosphere of oxygen, argon, nitrogen, or air, and excimer laser treatment with ArF or KrF. Among them, surface treatment with alkoxysilane and/or acid or alkaline treatment are preferred for uniformly activating the entire surface of the particle.

Alkoxysilane used as the surface treatment agent is not particularly limited, and examples thereof include dialkoxysilane, trialkoxysilane, and tetraalkoxysilane. Among them, tetraalkoxysilane is preferred because it has the largest number of alkoxysilyl groups in one molecule. Specific examples of tetraalkoxysilane include tetramethoxysilane, tetraethoxysilane, tetrapropoxysilane, tetrabutoxysilane, and tetraphenoxysilane. Those having a relatively small molecular weight give more alkoxysilyl groups to the surface of the core particle. Accordingly, tetramethoxysilane, tetraethoxysilane, and tetrapropoxysilane having an alkoxysilyl group having 3 or less carbon atoms are preferred, and tetraethoxysilane is more preferred from the viewpoint of availability. These alkoxysilanes are used alone or in combination of two or more thereof.

The method for activating the surface of the core particle with alkoxysilane is not particularly limited, but preferably a method wherein the particle and the alkoxysilane are stirred and mixed in a solution containing an alkali catalyst. For example, the core particle is dispersed in a solution containing an alkali catalyst and an alcohol to give a concentration of 0.05 to 10% by weight, and alkoxysilane dissolved in an alcohol is added to the dispersion medium. The ratio between the core particle and alkoxysilane is not particularly limited, but usually 0.01 to 10 mmol of alkoxysilane is used for 1 g of the core particle. The alcohol contained in the dispersion medium and the alcohol for dissolving alkoxysilane are not particularly limited. For example, ethanol, methanol, isopropanol, ort-butyl alcohol are used alone or in combination of two or more thereof. Among them, methanol is preferred because it readily dries and inexpensive.

The dispersion of the core particle mixed with the alkoxysilane solution is usually stirred at 0 to 50° C. for about 5 to 30 hours for surface treatment. The obtained core particle is washed, and then dried.

Under the above-described treatment conditions, dehydration condensation occurs between the alkoxysilyl group of alkoxysilane and the functional group on the surface of the core particle. At the same time, dehydration condensation of the alkoxysilyl groups to be grafted on the polymer compound may occur. Therefore, in order to sufficiently achieve the effect of surface treatment with alkoxysilane, it is effective that the core particle is treated with an acid or alkali after the above-described treatment. In particular, acid treatment is preferred for hydrolysis of a siloxane bond generated by dehydration condensation of alkoxysilyl groups. The method for treating the surface of the core particle with an acid is not particularly limited. For example, the core particle obtained by the above-described treatment is dispersed in a 0.01 to 3 N acid, and stirred for about 1 to 5 hours. The acid used for the treatment may be any known inorganic acid and/or organic acid. Examples of the inorganic acid include sulfuric acid, nitric acid, hydrochloric acid, and hydrofluoric acid, and examples of the organic acid include formic acid, acetic acid, and benzoic acid. Among them, inorganic acids are preferred because they allow relatively severe treatment conditions thereby completing the treatment within a short period of time, and hydrochloric acid is more preferred from the viewpoints of easiness of removal after treatment due to its high volatility, and relative easiness of handling.

As described above, the present invention provides a particle which has an excellent capability of fixing a biologically active substance. Furthermore, the nature of inhibiting the nonspecific adsorption of components other than the target protein to the particle is promoted by adding a component containing an alkylene glycol residue to the surface layer of the particle containing a polymer compound. In addition, the terminal reactive group of the polymer compound can be bonded to the core particle, which allows chemical grafting of the polymer compound. Accordingly, the layer containing the polymer compound will not be detached by washing. Furthermore, the amount of the polymer compound to be grafted is uniformly increased by activation of the surface of the core particle with alkoxysilane before the application of the polymer compound, which increases the amount of the biologically active substance fixed to the grafted particle. As a result of this, when a biologically active substance is bonded to the particle, substances (proteins and others) trapped by the biologically active substance are efficiently collected. In addition, the size and strength of the particle can be appropriately and readily controlled by appropriately selecting the core particle. Accordingly, the particle of the present invention is suitable as a carrier for fixing a biologically active substance, and can be used for various applications such as drug discovery and fillers for affinity chromatography.

EXAMPLES

Synthesis of
p-Nitrophenyloxycarbonyl-Polyethylene Glycol
Methacrylate (MEONP))

Into 20 mL of chloroform was dissolved 0.01 mol of polyethylene glycol monomethacrylate (Blenmer PE-200 manufactured by NOF Corp.), and then the solution was cooled to −30° C. While the temperature was maintained at −30° C., into this solution was slowly dropped a homogeneous solution prepared in advance and made of 0.01 mol of p-nitrophenyl chloroformate (available from Aldrich Co.), 0.01 mol of triethylamine (available from Wako Pure Chemical Industries, Ltd.), and 20 mL of chloroform. The reactive components were caused to react at −30° C. for 1 hour, and then the solution was further stirred at room temperature for 2 hours. Thereafter, salts are filtrated off from the reaction solution, and the solvent was removed so that crude p-nitrophenyloxycarbonyl-polyethylene glycol methacrylate (hereinafter referred to as MEONP) was obtained. The crude product was purified with a silica gel column. The resultant monomer was measured by $^1$H-NMR in a solution of heavy chloroform. As a result, it was confirmed that 4.5 units of ethylene glycol residues were contained.

Synthesis Example 1 of Polymer Compound

MEONP was dissolved in dehydrated ethanol to give a concentration of 1.0 mol/L. Furthermore, thereto were added (3-mercaptopropyl)trimethoxysilane (hereinafter referred to as MPDES and available from AZmax. Co) and 2,2-azobisisobutyronitrile (hereinafter referred to as AIBN and available from Wako Pure Chemical Industries, Ltd.) so as to set the concentration of each of these components to 0.07 mol/L. The solution was stirred until the solution turned into a homogeneous state. Thereafter, in the atmosphere of argon gas, the reactive components were caused to react at 60° C. for 24 hours, and then the reaction solution was dropped into diethylether. The resultant precipitation was then collected. The resultant polymer compound was measured by 1H-NMR in a solution of heavy chloroform, and then the composition ratio of this polymer compound was calculated from integral values of peaks appeared around 7.4 ppm and 8.3 ppm and assigned to the benzene ring of MEONP, a peak appeared around 0.7 ppm and assigned to the methylene bonded to Si in MPDES. As a result, it was confirmed that the composition ratios of MEONP and MPDES were 96 mol % and 4 mol %, respectively.

Synthesis Example 2 of Polymer Compound

Polyethylene glycol methyl ether methacrylate having a number-average molecular weight Mn of about 1100 (also known as methoxypolyethylene glycol methacrylate, which will be referred to as PEGMA1100 hereinafter, and was available from Aldrich Co.), and MEONP were dissolved in dehydrated ethanol, so as to prepare a monomer mixed solution. The total concentration of the monomers was 0.3 mol/L. About the mol ratio between the individual monomers, the ratio of PEGMA1100 to MEONP was 70 to 30. Furthermore, thereto were added MPDES and AIBN so as to set the concentration of each of these components to 0.003 mol/L. The solution was stirred until the solution turned into a homogeneous state. Thereafter, in the atmosphere of argon gas, the reactive components were caused to react at 60° C. for 6 hours, and then the reaction solution was dropped into diethylether. The resultant precipitation was then collected. The resultant polymer compound was measured by 1H-NMR in a solution of heavy ethanol, and then the composition ratio of this polymer compound was calculated from integral values of a peak appeared around 3.4 ppm and assigned to the terminal methoxy group of PEGMA, peaks appeared around 7.6 ppm and 8.4 ppm and assigned to the benzene ring of MEONP, and a peak appeared around 0.7 ppm and assigned to the methylene bonded to Si in MPDES. As a result, it was confirmed that the composition ratios of PEGMA, MEONP, and MPDES were 66 mol %, 34 mol %, and 0.7 mol %, respectively.

Example 1

The polymer compound of Synthesis Example 1 was dissolved in cyclohexanone to make a 0.3% by weight solution, into which silica beads (MB-1000, manufactured by Fuji Silysia Chemical Ltd.) having a particle size of 45 to 75 μm and a pore diameter of 100 nm was immersed, and thoroughly stirred with a vortex mixer. The beads were collected by suction filtration, thoroughly dried, and then heated at 150° C. for 2 hours.

Example 2

In the same way as in Example 1, the polymer compound of Synthesis Example 2 was applied to the beads, and then the beads were subjected to the heating treatment.

Example 3

Silica beads having an average particle size of 45 μm and a pore diameter of 5 to 7 nm (silica gel 60N, hereinafter referred to as Si60N, manufactured by Kanto Chemical Co., Inc.) were immersed in a 0.3% by weight cyclohexanone solution of the polymer compound of Synthesis Example 1, and thoroughly stirred with a vortex mixer. The beads were collected by suction filtration, thoroughly dried, and then heated at 150° C. for 2 hours.

Example 4

Si60N was immersed in a 10% by weight cyclohexanone solution of the polymer compound of Synthesis Example 1, and thoroughly stirred with a vortex mixer. The beads were collected by suction filtration, thoroughly dried, and then heated at 150° C. for 2 hours.

Example 5

In the same way as in Example 3, the polymer compound of Synthesis Example 2 was applied to the beads, and then the beads were subjected to the heating treatment.

Example 6

In the same way as in Example 4, the polymer compound of Synthesis Example 2 was applied to the beads, and then the beads were subjected to the heating treatment.

Example 7

Si60N was immersed in a 50% by weight cyclohexanone solution of the polymer compound of Synthesis Example 2, and thoroughly stirred with a vortex mixer. The beads were collected by suction filtration, thoroughly dried, and then heated at 150° C. for 2 hours.

Example 8

15 g of Si60N was dispersed in a solution containing 480 ml of methanol and 120 ml of 10% ammonia water. To the solution, a solution prepared by dissolving 3 mmol of tetraethoxysilane (synonym: tetraethyl orthosilicate, hereinafter referred to as TEOS, manufactured by Wako Pure Chemical Industries, Ltd.) in 12.7 ml of methanol was added dropwise. After stirring for 16 hours at room temperature, the supernatant was removed by centrifugation. The beads were dispersed again in methanol, and the operation of removing the supernatant by centrifugation was repeated three times. Thereafter, the beads were collected by suction filtration, and thoroughly dried. 10 g of the obtained silica beads was dispersed in 300 ml of 2N hydrochloric acid, and stirred for 2 hours at room temperature. The supernatant was removed by centrifugation, the beads were dispersed in ultrapure water, and the supernatant was removed by centrifugation. The operation was repeated several times until the supernatant was neutralized. Thereafter, the beads were dispersed in methanol, collected by suction filtration, and thoroughly dried. Subsequently, the polymer compound of Synthesis Examples 2 was applied to the silica beads in the same way as Example 1, and then the beads were subjected to the heating treatment.

(Evaluation of Nonspecific Adsorption)

About 20 mg of each of the beads of Examples 1 and 2 was treated with 1 mol/L 2-aminoethanol (solvent: dimethyl sulfoxide) at 40° C. overnight, whereby MEONP was inactivated. The beads were thoroughly dried, and then treated with 1 mL of a 45 mg/mL bovine serum albumin (BSA) solution in PBS at 4° C. for 17 hours. Thereafter, the supernatant was removed by centrifugation. PBS was added to the beads, thoroughly rinsed with a vortex mixer, and then the supernatant was removed. The operation was repeated three times. To the beads 2 mL of a 1% by weight sodium dodecyl sulfonate (SDS) solution in PBS was added, the mixture was allowed to stand for 1 hour, and then the BSA adsorbed to the particle surface was removed. The supernatant was collected and used as the measurement sample for by Micro-BCA assay. The Micro-BCA assay was conducted using a Micro BCA™ Pritein Assay Kit manufactured by PIERCE. The reagent is used to determine the concentration of protein in a dilute solution (0.5 to 20 μg/mL), and contains bicinchoninic acid as the chelating reagent for forming a color complex with cuprous ion in the presence of protein. A sample was prepared according to the standard protocol of the assay, and the amount of nonspecifically adsorbed BSA was determined at an absorbance of 562 nm.

(Removal of Polymer Compound not Chemically Bonded to Beads)

About 150 mg of each of the beads of Examples 1 to 8 was added to about 1.7 mL of dimethyl sulfoxide (hereinafter referred to as DMSO), thoroughly stirred with a vortex mixer, and then stirred for 1 hour in a thermostat shaker at 40° C. After the silica beads were precipitated, DMSO was refreshed, and the same operation was repeated twice. Thereafter, DMSO was replaced with ethanol, and thoroughly dried.

(Evaluation of Active Ester Equivalent)

About 20 mg of each of the beads obtained in the previous section was added to about 2 mL of an aqueous 0.01N sodium hydroxide solution. The mixture was thoroughly stirred with a vortex mixer, and allowed to stand at room temperature for 1 hour, whereby p-nitrophenol was liberated from MEONP. The supernatant was collected, and the active ester equivalent was calculated as described below from the absorbance at 400 nm.

A calibration curve of the absorbance of p-nitrophenol at 400 nm was prepared using an aqueous p-nitrophenol solution having a known concentration. The amount of p-nitrophenol liberated from the beads was calculated using the calibration curve, whereby the active ester equivalent per unit weight of the beads was determined.

Comparative Example 1

The silica beads used in Example 1 were used without applying the polymer compound, and the amount of adsorbed BSA was measured by Micro-BCA assay for the evaluation of nonspecific adsorption.

Table 1 lists the amount of adsorbed BSA for Examples 1 and 2, and Comparative Example determined by Micro-BCA assay. As is evident from Table 1, the amount of BSA adsorbed to the particles of the present invention was significantly lower than that adsorbed to the silica beads, which indicates that the nonspecific adsorption of the protein was inhibited. The beads of Example 2 containing PEGMA1100 as a copolymerization component adsorbed a smaller amount of BSA, which is likely due to the nonspecific adsorption inhibition effect of the polyethylene glycol chain.

TABLE 1

|  | Example 1 | Example 2 | Comparative Example 1 |
|---|---|---|---|
| Amount of adsorbed BSA (μg/mg) | 1.01 | 0.020 | 7.59 |

Table 2 lists the active ester equivalent of the beads prepared in Examples 1 and 2. As is evident from Table 2, MEONP remained on the particles of the present invention after washing with DMSO, which indicates that the particles still had a capability of fixing a biologically active substance. The beads of Example 1 exhibited a high active ester equivalent, which suggests that they can fix a larger amount of the biologically active substance.

TABLE 2

|  | Example 1 | Example 2 |
|---|---|---|
| Active Ester Equivalent (nmol/mg) | 8.3 | 3.1 |

Table 3 lists the active ester equivalent of the beads prepared in Examples 3 and 4. As is evident from Table 3, MEONP remained on the particles of the present invention after washing with DMSO, which indicates that the particles still had a capability of fixing a biologically active substance. The beads of Examples 3 and 4 were coated with the same amount of the polymer compound having the same components and the same composition ratios, but the beads of Example 4 exhibited a higher active ester equivalent than the beads of Example 3. This is likely due to that the amount of grafted polymer compound was increased by the treatment with the concentrated solution of the polymer compound. In particular, the beads of Example 4 exhibited a high active ester equivalent, which suggests that the beads can fix a larger amount of the biologically active substance.

TABLE 3

|  | Example 3 | Example 4 |
| --- | --- | --- |
| Active Ester Equivalent (nmol/mg) | 5.8 | 93.7 |

Table 4 lists the active ester equivalent of the beads prepared in Examples 5 to 7. As is evident from Table 4, MEONP remained on the particles of the present invention after washing with DMSO, which indicates that the particles still had a capability of fixing a biologically active substance. The beads of Examples 5 to 7 were coated with the same amount of the polymer compound having the same components and the same composition ratios, but the beads of Examples 7 exhibited the highest active ester equivalent, followed by the beads of Examples 6 and 5. In particular, the beads of Example 7 exhibited the highest active ester equivalent, which suggest that the beads can fix a larger amount of the biologically active substance. In addition, the beads are coated with the same polymer compound as Example 2, so that are expected to have nonspecific adsorption inhibition effect.

TABLE 4

|  | Example 5 | Example 6 | Example 7 |
| --- | --- | --- | --- |
| Active Ester Equivalent (nmol/mg) | 1.5 | 10.8 | 23.8 |

Table 5 lists the active ester equivalent of the beads prepared in Examples 5 and 8. As is evident from Table 5, MEONP remained on the particles of the present invention after washing with DMSO, which indicates that the particles still had a capability of fixing a biologically active substance. The beads of Examples 5 and 8 were coated with the same amount of the polymer compound having the same components and the same composition ratios, but the beads of Example 8 exhibited a higher active ester equivalent than the beads of Example 5. This is likely due to that the amount of grafted polymer compound was increased by the surface treatment with TEOS and the treatment with hydrochloric acid. The beads are expected to fix a larger amount of the biologically active substance. In addition, the beads are coated with the same polymer compound as Example 2, so that are expected to have nonspecific adsorption inhibition effect.

TABLE 5

|  | Example 5 | Example 8 |
| --- | --- | --- |
| Active Ester Equivalent (nmol/mg) | 1.5 | 4.5 |

The invention claimed is:

1. A particle comprising a polymer layer coating the surface of an inorganic core particle, wherein the polymer layer comprises a copolymer comprising repeating units derived from:
(a) a first repeating unit comprising an ethylenically unsaturated polymerizable monomer having an active ester functional group for fixing a biologically active substance, wherein said first repeating unit is represented by general formula [2]

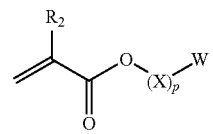

wherein $R_2$ represents a hydrogen atom or a methyl group, X represents an alkyl group or an alkylene glycol residue having 1 to 10 carbon atoms, W represents an active ester group, and p represents an integer from 1 to 100, and the repeated Xs may be the same or different, and p is an integer of 2 or more and 100 or less; and
(b) a second repeating unit comprising an ethylenically unsaturated polymerizable monomer having an alkylene glycol residue; wherein said second repeating unit is represented by the following general formula [3]

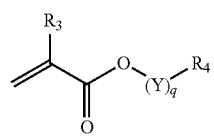

wherein $R_3$ represents a hydrogen atom or a methyl group, $R_4$ represents a hydrogen atom or an alkyl group having 1 to 20 carbon atoms, Y represents an alkylene glycol residue having 1 to 10 carbon atoms, and q represents an integer from 1 to 100, the repeated Ys may be the same or different; and
additionally wherein the copolymer has a reactive functional group represented by the following general formula [5]

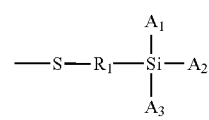

on at least one terminal side thereof, and wherein the copolymer is covalently bonded to the surface of the core particle through said reactive functional group, and wherein at least one of $A_1$, $A_2$ and $A_3$ is a reactive moiety that is covalently bound to the surface of the inorganic core particle; the others are each an alkyl group; and $R_1$ is an alkylene group having 1 to 20 carbon atoms.

2. The particle according to claim 1, wherein the copolymer further comprises a third repeating unit derived from an ethylenically unsaturated polymerizable monomer having a hydrophobic group.

3. The particle according to claim 1, wherein the active ester group of the first repeating unit of the polymer is a p-nitrophenyl ester or N-hydroxysuccinimide ester.

4. The particle according to claim 1, wherein the second repeating unit is methoxypolyethylene glycol (meth)acrylate or ethoxypolyethylene glycol (meth)acrylate.

5. The particle according to claim 4, wherein the average repeating number of the ethylene glycol residue of the methoxypolyethylene glycol (meth)acrylate or ethoxypolyethylene glycol (meth)acrylate is from 3 to 100.

6. The particle according to claim 2, wherein the third repeating unit is a monomer selected from the group consisting of n-butyl methacrylate, n-dodecyl methacrylate, n-octyl methacrylate, and cyclohexyl methacrylate and combinations thereof.

7. The particle according to claim 1, wherein the inorganic core particle is composed of an inorganic oxide.

8. The particle according to claim 7, wherein the inorganic oxide is silicon oxide or titanium oxide.

9. The particle according to claim 1, wherein W is a p-nitrophenyl active ester group, a phthalic imide active ester group, or a 5-norbornene-2, 3-dicarboxyimide active ester group.

\* \* \* \* \*